United States Patent [19]

Tomita et al.

[11] 4,201,781
[45] May 6, 1980

[54] SUBSTITUTED 7[S-OXOPYRIDO[2,3-D]PYRIMIDINE CARBOXAMIDO ACETAMIDO]CEPHALOSPORINS

[75] Inventors: Masatsugu Tomita, Nagaokakyo; Yoshiyuki Takase, Amagasaki; Toshio Komiya, Izumi-ohtsu, all of Japan

[73] Assignee: Dainippon Pharmaceutical Co., Ltd., Osaka, Japan

[21] Appl. No.: 973,169

[22] Filed: Dec. 26, 1978

[30] Foreign Application Priority Data

Dec. 28, 1977 [JP] Japan .................. 52-158398

[51] Int. Cl.$^2$ .................. A61K 31/545; C07D 501/36
[52] U.S. Cl. ...................... 424/246; 544/27; 544/28; 544/279
[58] Field of Search .................. 544/27; 424/246

[56] References Cited

U.S. PATENT DOCUMENTS

| 4,015,000 | 3/1977 | Kocsis et al. | 544/25 |
| 4,041,161 | 8/1977 | Kocsis et al. | 544/25 |
| 4,061,748 | 12/1977 | Yamada et al. | 424/246 |
| 4,138,554 | 2/1979 | Naito et al. | 544/22 |

FOREIGN PATENT DOCUMENTS 808906  4/1974 Belgium .
833063  3/1976 Belgium .
851983  7/1977 Belgium .

Primary Examiner—David Wheeler
Attorney, Agent, or Firm—Wenderoth, Lind & Ponack

[57] ABSTRACT

Cephalosporin compounds of the formula

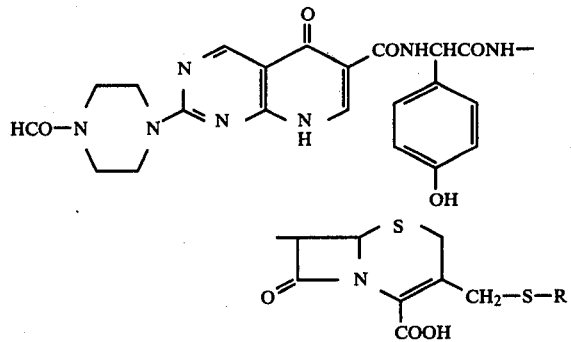

wherein R is 1-carboxymethyl-1,2,3,4-tetrazol-5-yl or 5-carboxymethyl-1,3,4-thiadiazol-2-yl, and non-toxic pharmaceutically acceptable salts thereof, and processes for preparing them. The compounds have superior antibacterial activity and excellent solubility in an aqueous medium, and are useful as antibacterial agent.

10 Claims, No Drawings

SUBSTITUTED 7[S-OXOPYRIDO[2,3-D]PYRIMIDINE CARBOXAMIDO ACETAMIDO]CEPHALOSPORINS

This invention relates to novel cephalosporin compounds. Specifically, the invention relates to novel cephalosporin compounds having superior antibacterial activity, and excellent solubility in an aqueous medium, injectable solutions containing the novel cephalosporin compounds, preparations for formulating the solutions, and to processes for preparing the novel cephalosporin compounds.

The novel cephalosporin compounds provided by the invention are compounds of the following formula

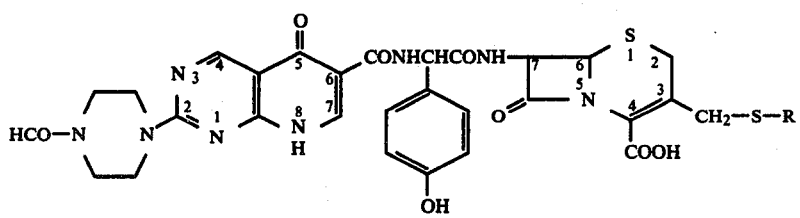

wherein R is 1-carboxylmethyl-1,2,3,4-tetrazol-5-yl or 5-carboxymethyl-1,3,4-thiadiazol-2-yl,
and their non-toxic pharmaceutically acceptable salts.

The non-toxic pharmaceutically acceptable salts are salts formed between the cephalosporin compounds of formula [I] and non-toxic pharmaceutically acceptable inorganic or organic bases. Preferred non-toxic salts are alkali metal salts such as sodium and potassium salts, the former being particularly preferred.

The cephalosporin compounds of formula [I] exist in two types (keto-type and enol-type) of formula [I] and [I'] as shown below. In the present specification, these isomers are inclusively expressed by the ketotype of formula [I] below.

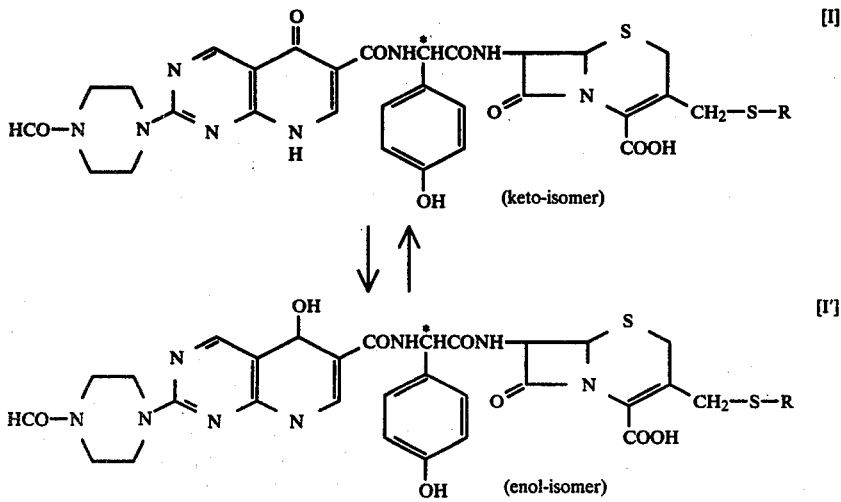

Since the asterisked carbon atom ascribable to the α-carbon of p-hydroxyphenylglycyl residue in formulae [I] and [I'] is an asymmettic carbon, the cephalosporin compounds of the invention expressed by the formula [I], on the basis of the steric configuration concerning this carbon, include a D-isomer, an L-isomer, and a mixture of these isomers (to be referred to as D,L mixture). All of these isomers and mixture are expressed by formula [I] given hereinabove.

Sometimes, the cephalosporin compounds of formula [I] exist in the form of hydrates, and such hydrates are also included within the cephalosporin compounds of the invention expressed by formula [I].

Belgian Pat. No. 833,063, for example, disclose many N-acylcephalosporin derivatives resulting from the acylation of the α-amino group of 7-(α-amino-α-p-hydroxyphenylacetamido)cephalosporin derivatives with certain heterocyclic carboxylic acids. Sodium 7-{α-[5,8-dihydro-2-(1-piperazinyl)-5-oxopyrido[2,3-d]pyrimidine-6-carboxamido]-α-p-hydroxyphenylacetamido}-3-(1-methyl-1,2,3,4-tetrazol-5-yl)thiomethyl-3-cephem-4-carboxylate, which appears to be most similar in chemical structure to the compound of formula [I] of the present invention among the compounds specifically disclosed in the above Belgian patent, exhibits superior antibacterial activity as the compound of the present invention, but has the defect that it has extremely low solubility in water, and there is a question about the feasibility of its practice as a medicine as described hereinafter.

An object of this invention is to provide novel cephalosporin compounds having superior antibacterial activity against Gram-negative and Gram-positive bacteria and being highly soluble in water, and a process for their preparation.

Another object of this invention is to provide novel cephalosporin compounds having superior antibacterial activity against Pseudomonas aeruginosa and some of cephalexin-resistant bacteria.

Still another object of this invention is to provide injectable compositions for intramuscular, intravenous or subcutaneous administration containing these compounds.

Other objects and advantages of this invention will become apparent from the following description.

The novel cephalosporin compounds of the invention are inclusively expressed by formula [I], but are individually expressed by the following formulae [Ia] and [Ib].

Formula [Ia]

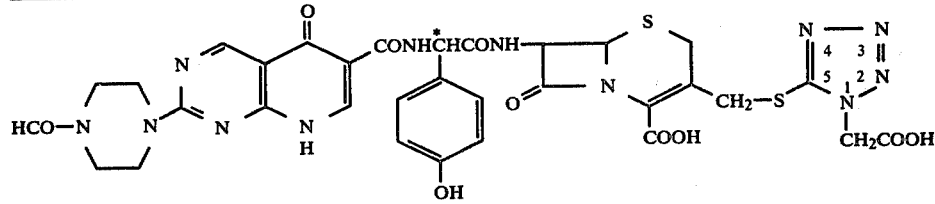

Formula [Ib]

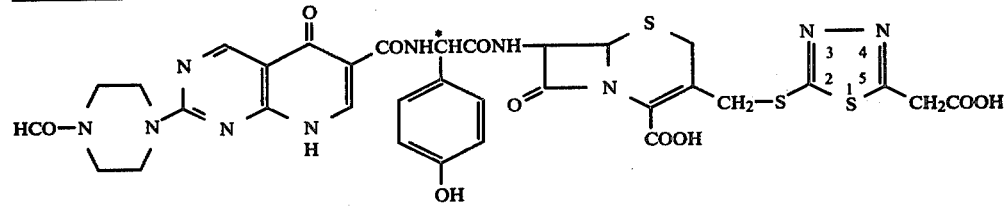

The asterisked carbon atom in each of formulae [Ia] and [Ib] is an asymmetric carbon atom, and on the basis of its steric configuration, each includes a D-isomer, L-isomer, and a D,L-mixture. D-isomers show especially superior antibacterial activity and low toxicity, and are named as follows:

Compound of the formula [Ia]

7-{D-α-[5,8-dihydro-2-(4-formyl-1-piperazinyl)-5-oxopyrido[2,3-d]pyrimidine-6-carboxamido]-α-p-hydroxyphenylacetamido}-3-(1-carboxymethyl-1,2,3,4-tetrazol-5-yl)thiomethyl-3-cephem-4-carboxylic acid.

Compound of the formula [Ib]

7-{D-α-[5,8-dihydro-2-(4-formyl-1-piperazinyl)-5-oxopyrido[2,3-d]pyrimidine-6-carboxamido]-α-hydroxyphenylacetamido}-3-(5-carboxymethyl-1,3,4-thiadiazol-2-yl)thiomethyl-3-cephem-4-carboxylic acid.

Pharmaceutically acceptable salts, especially sodium and potassium salts, of these compounds are equally active.

The novel cephalosporin compounds of formula [I] and their non-toxic pharmaceutically acceptable salts can be produced by processes described hereinbelow.

Process (a):

The outline of the process (a) can be shown by the following reaction scheme.

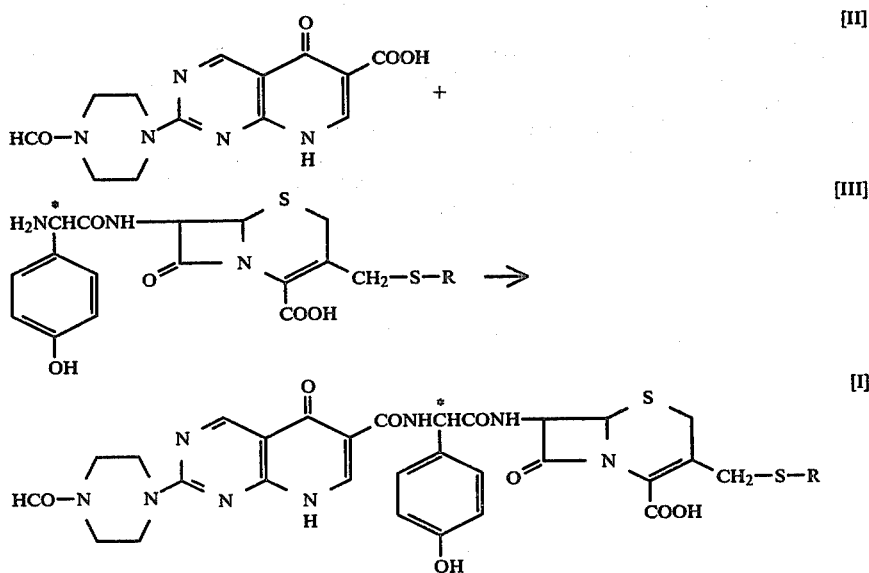

wherein R is the same as defined above.

According to the process (a), the novel cephalosporin compound of this invention of formula [I] or its non-toxic pharmaceutically acceptable salt is prepared by reacting a compound [II] or its inorganic or organic salt, or its reactive derivative at the carboxyl group, with a compound [III], or its inorganic or organic salt or a derivative convertible to the compound [III] by hydrolysis or catalytic hydrogenation in an aqueous or non-aqueous medium, then if desired hydrolyzing or catalytically hydrogenolyzing the reaction product to form a cephalosporin compound of this invention, and if further desired, converting the reaction product to a non-toxic pharmaceutically acceptable salt.

The reactive derivatives at the carboxyl group of the formula [II] include all reactive derivatives known and used in the field of producing cephalosporins. Specific examples are its acid anhydrides formed with acids such as alkylcarbonic acids (e.g., ethylcarbonic acid, isopropylcarbonic acid, iso- or sec-butylcarbonic acid), alkylcarboxylic acids (e.g., pivalic acid, pentanoic acid, isopentanoic acid, 2-ethylbutyric acid, and 2-ethylhexanoic acid), phosphoric acids (e.g., diethylphosphoric acid), and sulfonic acids (e.g., methanesulfonic acid); its reactive esters such as the p-nitrophenyl ester, trichlorophenyl ester, p-nitrophenylthio ester, N-hydroxypiperidine ester, N-hydroxysuccinimide ester or N-hydroxyphthalimide ester; its reactive amides such as N-carbonylimidazole or N-carbonyltetrazole; its acid halides such as acid chloride; and its acid azides.

The derivatives convertible to the compound [III] by hydrolysis or catalytic hydrogenation are well known in the field of producing semi-synthetic cephalosporin, and can be used in the process (a) of this invention. Typical examples of such derivatives are trimethylsilyl ester, trityl ester, p-nitrobenzyl ester, and phenacyl ester. Derivatives obtained by protecting the hydroxy group of the benzene nucleus of the compound [III] by, for example, an ethoxycarbonyl or benzyloxycarbonyl group can also be used.

The inorganic or organic salts of the compound [II] and/or of the compound [III] include alkali metal salts such as sodium or potassium salts, and salts with organic bases such as triethylamine or N-ethylmorpholine.

The above reaction is carried out at −40° to 40° C. for 1 to 10 hours in a solvent, preferably in the presence of a base. The solvent, base and other reaction conditions which may be used are substantially the same as those used in the chemistry of cephalosporin.

For example, when an anhydride derived from the compound [II] and ethyl chloroformate is used, the reaction is performed under cooling or at room temperature in the presence of a tertiary amine such as triethylamine or N,N-dimethylaniline in an inert solvent such as acetone, tetrahydrofuran, dimethylformamide, chloroform, dichloromethane or hexamethylphosphoramide, a mixture of such inert solvents, water, or a hydrous organic solvent.

carbonate in dimethylformamide, dichloromethane, dioxane, water or a mixture of these solvents.

The reaction of the compound [II] or its salt with the compound [III] or its salt is advantageously performed in the presence of a condensing agent such as N,N'-dicyclohexylcarbodiimide.

When the compound [II] or its salt or its reactive derivative at the carboxyl group is reacted with a derivative convertible to the compound [III], a reaction product having a moiety of the compound [III] convertible to the cephalosporin compound of this invention is sometimes formed according to reaction conditions. For example, it is when the carboxyl group of the reaction product is in the form of an ester such as a silyl ester, or when the hydroxyl group at the benzene nucleus of the reaction product is protected by a protective group such as an acyl group. In such a case, the product is further hydrolyzed or catalytically hydrogenolyzed in a customary manner known in the chemistry of cephalosporin to form the cephalosporin compound of this invention.

Since the asterisked carbon atom ascribable to the α-carbon of p-hydroxyphenylglycyl residue in formula [III] in the reaction scheme (a) is an asymmetric carbon atom, the compound [III] includes an D-isomer, an L-isomer and a D,L-mixture.

If the D-isomer of the compound [III] is used as a starting material in the process (a), the corresponding cephalosporin compound of this invention can be obtained in a D-form. If, the D,L-mixture of the compound [III] is used as a starting material, a cephalosporin compound of this invention in a D,L-mixed form is obtained. As stated hereinabove, the novel cephalosporin compounds of this invention in a D-form have especially high antibacterial activities.

Hence, in the process (a), the type of the isomer of the compound [III] used as a starting material is selected according to the desired isomer of the final product.

Process (b)

The novel cephalosporin compounds of this invention can also be produced by the process (b) mentioned below. The outline of the process (b) can be expressed by the following reaction scheme (b).

Reaction scheme (b)

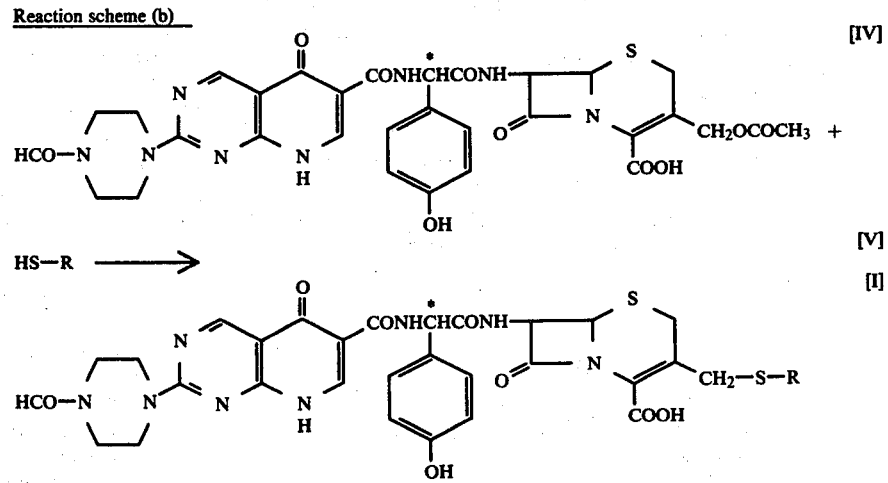

When an N-hydroxysuccinimide ester of the compound [II] is used, the reaction is performed at 0° to 10° C. for 1 to 2 hours in the presence of a base such as triethylamine, lutidine, sodium hydroxide, or sodium wherein R is the same as defined above.

According to the process (b), the novel cephalosporin compound of this invention of formula [I] or its non-toxic pharmaceutically acceptable salt is prepared by reacting a compound [IV] or its inorganic or organic salt, or its derivative convertible to the compound [IV] by hydrolysis or catalytic hydrogenation with a compound [V] or its inorganic or organic salt, then optionally hydrolyzing or catalytically hydrogenating the reaction product, and further if desired converting the reaction product to a non-toxic pharmaceutically acceptable salt.

As the salt of the compound [IV] or the derivative convertible to the compound [IV] by hydrolysis or catalytic hydrogenation, there can be used the same salt or derivative as described above with regard to the compound [III] in the process (a).

The process (b) is carried out at 50° to 80° C. for 3 to 24 hours, preferably 5 to 10 hours, in a solvent such as water, hydrous acetone, buffer solution (pH 6 to 7) or the like. Generally, the reaction is carried out in the presence of catalyst such as potassium iodide and potassium thiocyanate in order to promote the reaction.

When the derivative convertible to the compound of formula [IV] is reacted with the compound of formula [V], an OH— and/or COOH— protected derivative of the compound of formula [I] can be obtained as described with regard to process (a). The product can be converted to the desired compound by hydrolysis or catalytic hydrogenation in the same way as described in regard to process (a).

The cephalosporin compound obtained by the above two procedures can be either in the free state or in the form of salt depending upon the selection of the starting compound and the reaction conditions, etc. The free state cephalosporin compound can be converted to a salt by treatment with an inorganic or organic base, in particular alkali metal compounds. The alkali metal compounds may be sodium 2-ethyl hexanoate, sodium hydroxide, sodium carbonate, potassium 2-ethyl hexanoate, potassium hydroxide, potassium carbonate and the like. The salt, on the other hand, is treated with an acid, if desired, to form a free state.

The isolation, purification, extraction, recrystallization, salt formation and other post-treatments of the product are performed in accordance with customary procedures in the chemistry of cephalosporin.

The starting compound of formula [II] employed in the process (a) can be obtained intramolecularly cyclizing a compound of the general formula

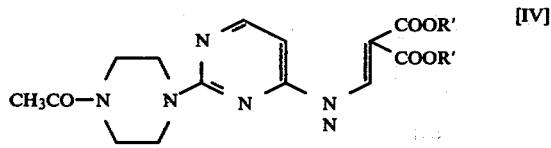 [IV]

wherein R' is an alkyl group containing 1 to 6 carbon atoms,
to form a compound of the general formula

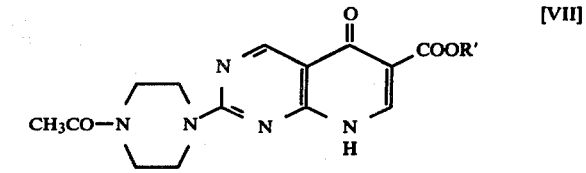 [VII]

wherein R' is the same as defined above,
hydrolyzing the compound [VII] to form a compound of the formula

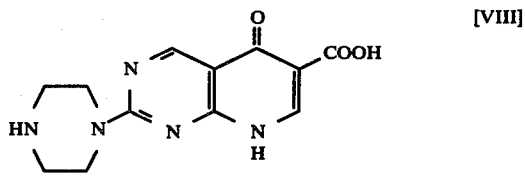 [VIII]

and then formylating the compound [VIII].

The formylation can be performed by suspending the compound of formula [VIII] in a formylating agent such as a mixture of acetic anhydride and formic acid or a mixture of formic acid and formamide, and heating it at 60° to 90° C. for 2 to 3 hours.

The intramolecular cyclization reaction of converting the compound of formula [VI] to the compound of formula [VII] and the hydrolysis of converting the compound of formula [VII] to the compound of formula [VIII] can be performed in accordance with the disclosure of U.S. Pat. No. 3,887,557.

The starting compounds of formula [III] used in process (a) are known, and can be prepared, for example, by the method disclosed in Belgian Patent No. 832,725.

The starting compound of formula [IV] used in the process (b) can be obtained by reacting a compound [II] with 7-(α-amino-p-hydroxyphenylacetoamido)-cephalosporanic acid in the same manner as in process (a).

The novel cephalosporin compounds of this invention, as will be shown in Examples to be given hereinbelow, have superior antibacterial activities and low toxicity and are highly soluble in water. Accordingly, these compounds can be used as drugs for the treatment, or prevention of bacterial infections of warm-blooded animals including man.

The dose of the cephalosporin compound of the invention in administration to man should be adjusted accoding to the age, body weight, and condition of the patient, the administering route, the number of administrations, etc. Usually, the dose for adults is 0.1 to 10 g/day, preferably 0.2 to 2 g/day. In view of their pharmacological properties described hereinafter, the cephalosporin compounds of this invention are desirably administered parenterally (e.g., intravenously, intramuscularly, or subcutaneously) in the form of an injectable solution dissolved in a pharmaceutically acceptable liquid medium.

The preparations for injectable solutions containing the cephalosporin compounds of this invention are, for example, an injecting set consisting of a vial filled with the cephalosporin compound as an active ingredient an ampoule containing an aqueous liquid medium capable of dissolving the active ingredient to form an injection, or an injection prepared by dissolving the active ingredient in an aqueous liquid medium. The aqueous liquid media are those which are usually employed in penicillin or cephalosporin preparations for injection, for example sterilized deionized water containing a known pH adjuster and osmotic pressure adjuster, and if required, a stabilizer. If desired, these preparations may further contain other pharmaceutically active ingredients and/or adjuvants according to the purpose of medication.

The processes for producing the novel cephalosporin compounds of the invention and the pharmacological actions of these compounds will be illustrated in greater detail.

Referential Examples 1 and 2 show the production of starting compounds for producing the compounds of the invention. Examples 1 to 4 illustrate the preparation of the novel cephalosporin compounds of the invention. Example 5 shows the production of pharmaceuticals comprising the cephalosporin compounds of the invention. Examples 6 to 9 and Tables I to IV show the biological activities, water-solubilities and toxicities of the compounds of the invention in comparison with those of two selected known compounds.

REFERENTIAL EXAMPLE 1

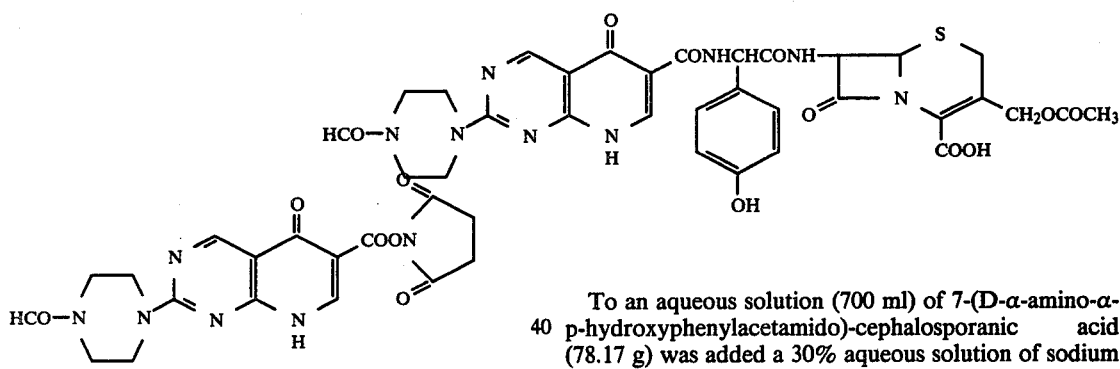

To diphenyl ether (16 ml) kept at 250°–255° C. was added with stirring diethyl N-[2-(4-acetyl-1-piperazinyl)-4-pyrimidinyl]-aminomethylenemalonate (2.0 g). The mixture was gently refluxed for 10 minutes, and then allowed to cool to room temperature. To the mixture was added n-hexane (12 ml). The resulting precipitate was collected, washed with ethanol, and recrystallized from ethanol to yield ethyl 2-(4-acetyl-1-piperazinyl)-5,8-dihydro-5-oxopyrido[2,3-d]pyrimidine-6-carboxylate (1.52 g), m.p. 300°–302° C. (decomp.).

A suspension of ethyl 5,8-dihydro-2-(4-acetyl-1-piperazinyl)-5-oxopyrido[2,3-d]pyrimidine-6-carboxylate (1000 g) and concentrated hydrochloric acid (800 ml) in a mixture of water (1200 ml) and ethanol (1000 ml) was refluxed for 8 hours and allowed to stand overnight. The crystals precipitated were collected, washed with ethanol, and dissolved by heating in an aqueous solution (10 liters) of sodium hydroxide (250 g). The solution was filtered, adjusted to pH 7–8 with acetic acid, and allowed to stand overnight with ice-cooling. The crystalline precipitate was collected, washed with water, and dried at 110° C. to give 5,8-dihydro-2-(1-piperazinyl)-5-oxopyrido [2,3-d]pyrimidine-6-carboxylic acid (625 g), m.p. 299°–305° C. (decomp.).

Formic acid (140 ml) was added dropwise to acetic anhydride (200 ml) cooled on an ice both. The solution was heated at 50° C. for 15 minutes and then cooled to 5° C. To the solution, 5,8-dihydro-2-(1-piperazinyl)-5-oxopyrido[2,3-d]pyrimidine-6-carboxylic acid (70 g) was added. The mixture was heated at 80° C. for 3 hours and then cooled. The crystals precipitated were collected by filtration and washed with ethyl ether to give 5,8-dihydro-2-(4-formyl-1-piperazinyl)-5-oxopyrido [2,3-d]pyrimidine-6-carboxylic acid (72.5 g). m.p. above 300° C.

A suspension of 5,8-dihydro-2-(4-formyl-1-piperazinyl)-5-oxopyrido[2,3-d]pyrimidine-6-carboxylic acid (273 g) and triethylamine (299 ml) in dried dichloromethane (3500 ml) was stirred well at room temperature for one hour. To the suspension, isopropyl chloroformate (221 g) was added dropwise with cooling at 0°–10° C. and the reaction mixture was stirred for 2 hours. A solution of N-hydroxysuccinimide (207 g) in dimethylformamide (350 ml) was added to the mixture and the resulting mixture was kept at 5°–10° C. for an additional 2 hours. The crystalline product was collected by filtration and washed successively with water (2000 ml) and acetone (2000 ml) to give N-[5,8-dihydro-2-(4-formyl-1-piperazinyl)-5-oxopyrido[2,3-d]pyrimidine-6-carbonyloxy]succinimide (326 g). m.p. above 300° C.

REFERENTIAL EXAMPLE 2

To an aqueous solution (700 ml) of 7-(D-α-amino-α-p-hydroxyphenylacetamido)-cephalosporanic acid (78.17 g) was added a 30% aqueous solution of sodium hydroxide to adjust its pH to 9.5 at 0°–2° C. with cooling and stirring. To the solution N-[5,8-dihydro-2-(4-formyl-1-piperazinyl)- 5-oxopyrido[2,3-d]pyrimidine-6-carbonyloxy]succimide (68.0 g) was added and the resulting mixture was kept for two hours with adjusting to pH 9.5 with 10% sodium hydroxide. The pale yellow crystals were collected by filtration and washed with acetone (1,000 ml) and diethyl ether (1,000 ml).

The pale yellow crystals (110.0 g) was dissolved in a mixture of water (1,800 ml) and acetone (2,700 ml) and the solution adjusted to pH 2.0 with hydrochloric acid. The resulting precipitate was collected by filtration, washed with acetone (1,000 ml) and diethyl ether (1,000 ml) to give 7-{D-α-[5,8-dihydro-2-(4-formyl-1-piperazinyl)-5-oxopyrido[2,3-d]pyrimidine-6-carboxamido]-p-hydroxyphenylacetamido}cephalosporanic acid (100.0 g)

IR (KBr): ν c=o 1780, 1720 cm$^{-1}$

NMR (DMSO, d$_6$, δ):

2.03 (3H, s, —OCOCH$_3$), 4.68, 5.01 (2H, ABq,

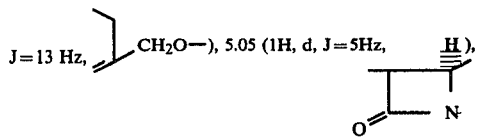

5.76 (1H, dd, J=5Hz, J=8Hz, H̲ ), 5.71(1H, d, J=8Hz, —CH— ), 8.12 (1H, s, HCO—), 9.30 (1H, d, J=8Hz, —CONH— ), 10.50 (1H, d, J=8Hz, CONH—), 9.14 (1H, s, H ).

EXAMPLE 1

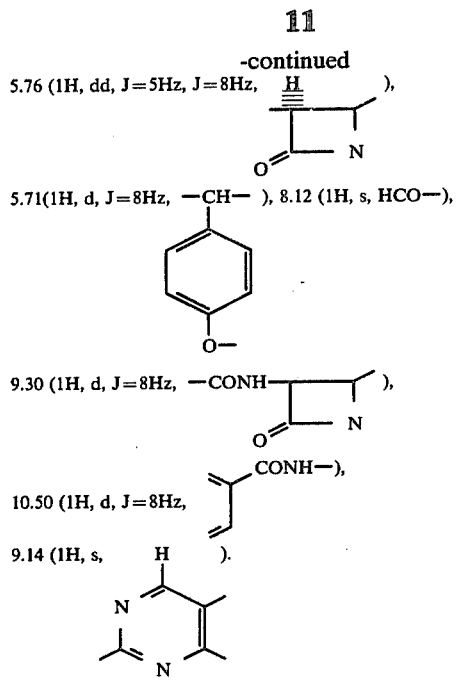

To a solution of 7-[D-α-amino-α-p-hydroxyphenylacetamido)-3-(1-carboxymethyl-1,2,3,4-tetrazol-5-yl) thiomethyl-3-cephem-4-carboxylic acid (2.26 g) and triethylamine (0.67 ml) in dried dimethylformamide (40 ml), N-[5,8-dihydro-2-(4-formyl-1-piperazinyl)-5-oxopyrido [2,3-d]pyrimidine-6-carbonyloxy]succimide (1.6 g) was added at 2°–4° C. The mixture was stirred for 3.5 hours and then filtered. The filtrate was poured into acetone (250 ml) and the resulting precipitate was collected by filtration, washed with acetone (100 ml) and diethyl ether (100 ml) and dissolved in ice water (30 ml). The aqueous solution was acidified with 10% hydrochloric acid and the crystals precipitated were collected, washed well with water and dissolved in a 2% sodium hydroxide solution. The solution was adjusted to pH 6.5 and filtered. The filtrate was lyophilized to give disodium 7-{D-α-[5,8-dihydro-2-(4-formyl-1-piperazinyl)-5-oxopyrido[2,3-d]pyrimidine-6-carboxamido]-α-p-hydroxyphenylacetamido}-3-(1-carboxylatometh yl-1,2,3,4-tetrazol-5-yl)thiomethyl-3-cephem-4-carboxylate (2.70 g).

IR (KBr): ν c=o 1770 cm$^{-1}$
NMR (DMSO, d$_6$, δ):

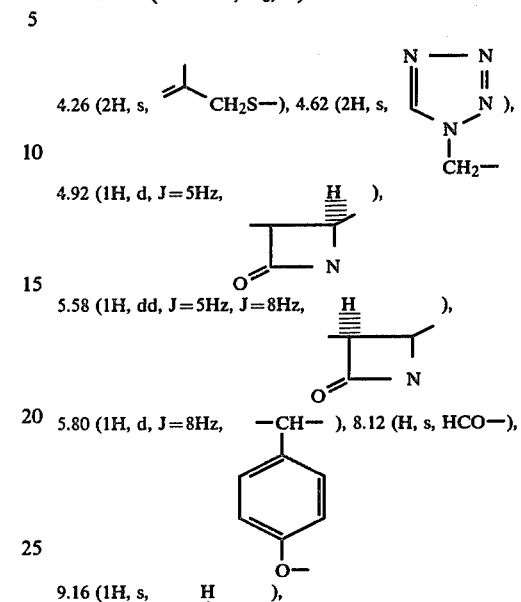

4.26 (2H, s, CH$_2$S—), 4.62 (2H, s, ... ), 4.92 (1H, d, J=5Hz, H̲ ), 5.58 (1H, dd, J=5Hz, J=8Hz, H̲ ), 5.80 (1H, d, J=8Hz, —CH— ), 8.12 (H, s, HCO—), 9.16 (1H, s, H ), 9.20 (1H, d, J=8Hz, —CONH— ), 10.61 (1H, d, J=8Hz, CONH—).

EXAMPLE 2

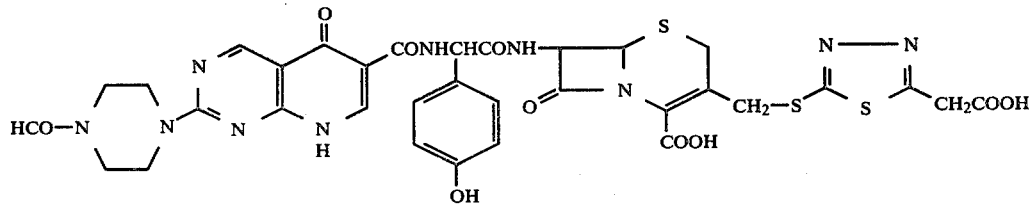

By the same procedure as described in Example 1, 7-{D-α-[5,8-dihydro-2-(4-formyl-1-piperazinyl)-5-oxopyrido[2,3-d]pyrimidine-6-carboxamido]-α-p-hydroxyphenylacetamido}-3-(5-carboxymethyl-1,3,4-thiadiazol-2-yl)thiomethyl-3-cephem-4-carboxylic acid was obtained from N-[5,8-dihydro-2-(4-formyl-1-piperazinyl)-5-oxopyrido[2,3-d]pyrimidine-6-car bonyloxy]succinimide and 7-(D-α-p-hydroxy-phenylacetamido)-3-(5-carboxymethyl-1,3,4-thiadiazol-2-yl)thiomethyl-3-cephem-4-carboxilic acid.

IR (KBr): ν c=o 1770 cm$^{-1}$
NMR (DMSO)-d$_6$, δ):

water, acetone and diethyl ether and dried to give 7-{D--α-[5,8-dihydro-2-(4-formyl-1-piperazinyl)-5-oxopyrido[2,3-d]pyrimidine-6-carboxamido]-α-p-hydroxyphenylacetamido}-3-(1-carboxymethyl-1,2,3,4-tetrazol-5-yl)thiomethyl-3-cephem-4-carboxylic acid (11.3 g).

IR (KBr): ν c=o 1770 cm$^{-1}$
NMR (DMSO-d$_6$, δ):

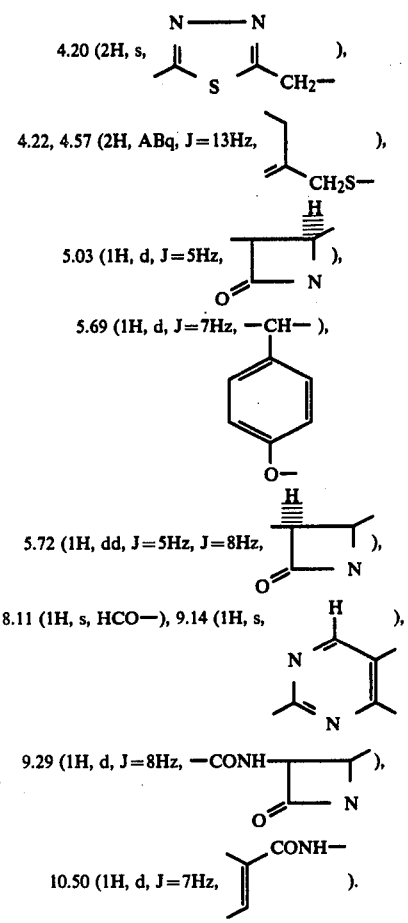

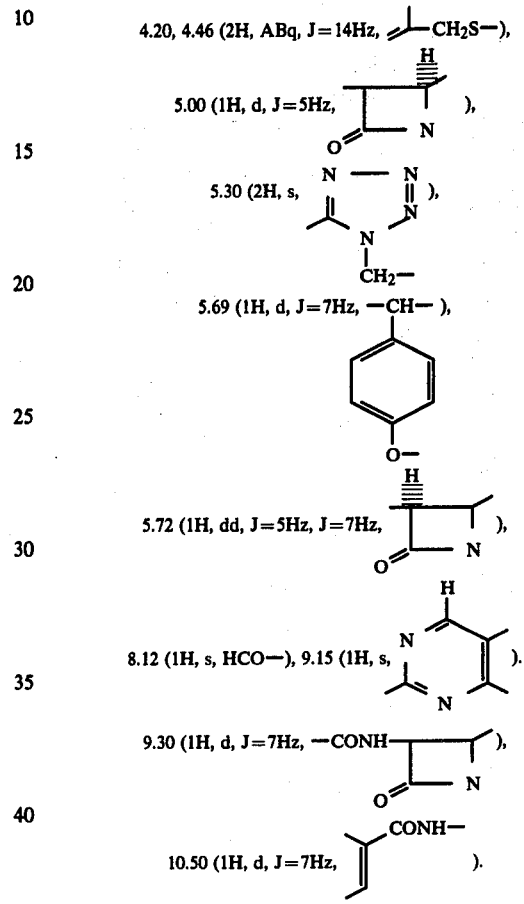

EXAMPLE 3

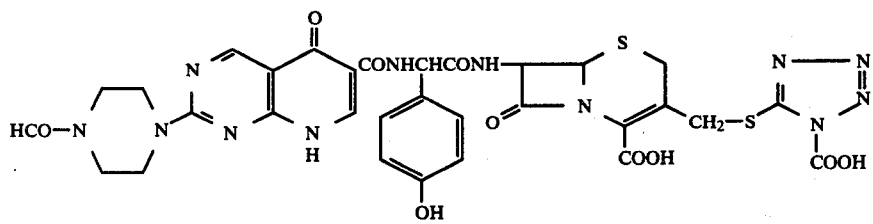

To a suspension of 7-{D-α-[5,8-dihydro-2-(4-formyl-1-piperazinyl)-5-oxopyrido[2,3-d]pyrimidine-6-carboxamido]-α-p-hydroxyphenylacetamido}-cephalosporanic acid (21.0 g) in pH 6.4 phosphate buffer (500 ml) were added sodium bicarbonate (10.8 g) and 5-mercapto-1,2,3,4-tetrazol-5-yl acetic acid (7.20 g), and the resultant solution was heated at 80° C. for 40 minutes with stirring. The reaction mixture was cooled in an ice bath and acidified with 10% hydrochloric acid. The resulting precipitate was collected by filtration, washed with The pale yellow acid (11.3 g) was dissolved in an enough volume of a 4% sodium hydroxide solution to adjust the pH to 6.5. The aqueous solution was filtered and the filtrate was lyophilized to give disodium 7-{D-α-[5,8-dihydro-2-(4-formyl-1-piperazinyl)-5-oxopyrido[2,3-d]pyrimidine-6-carboxamido]-α-p-hydroxyphenylacetamido}-3-(1-carboxylatomethyl-1,2,3,4-tetrazol-5-yl)thiomethyl-3-cephem-4-carboxylate (11.5 g).

This compound was determined to be identical with the compound of Example 1 by comparison of IR and NMR spectra.

EXAMPLE 4

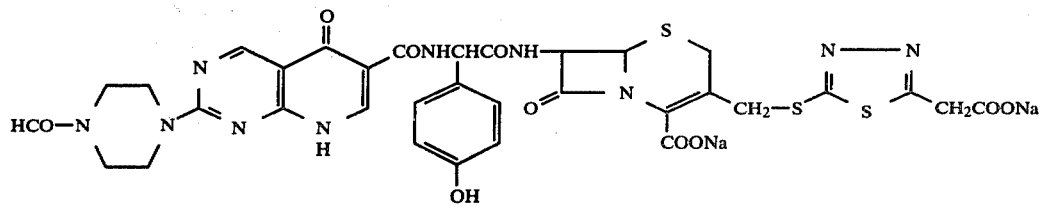

By the same procedure as described in Example 3, disodium 7-{D-α-[5,8-dihydro-2-(4-formyl-1-piperazinyl)-5-oxopyrido[2,3-d]pyrimidine-6-carboxamido]-α-p-hydroxyphenylacetamido}-3-(5-carboxylatomethyl-1,3,4-thiadiazol-2-yl)thiomethyl-3-cephem-4-carboxylate was obtained from 7-{D-α-[5,8-dihydro-2-(4-formyl-1-piperazinyl)-5-oxopyrido[2,3-d]pyrimidine-6-carboxamido]-α-p-hydroxyphenylacetamido}-3-acetoxymethyl-3-cephem-4-carboxylic acid and 2-mercapto-5-carboxymethyl-1,3,4-thiadiazole.

IR (KBr): $\nu$ c=o 1760 cm$^{-1}$

NMR (DMSO-d$_6$, δ):

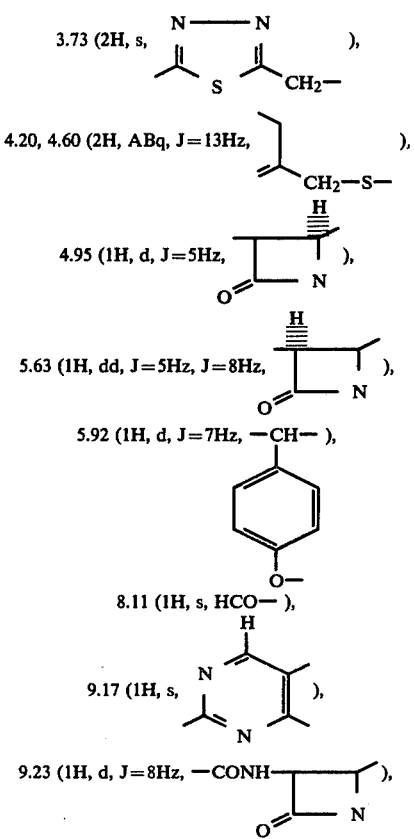

-continued

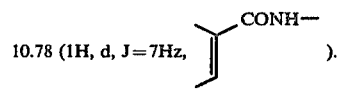

10.78 (1H, d, J=7Hz,

EXAMPLE 5 (Preparation of pharmaceutical)

(1) In an aseptic area, disodium 7-{D-α-]5,8-dihydro-2-(4-formyl-1-piperazinyl)-6-oxopyrido[2,3-d]pyrimidine-6-carboxamido]-α-p-hydroxyphenylacetamido}-3-(1-carboxylatomethyl-1,2,3,4-tetrazol-5-yl)thiomethyl-3-cephem-4-carboxylate (251 g) was dissolved in 2008 ml of distilled water for injection. The solution was filtered by a Millipore filter (pore size 0.22 micron; product of Millipore Corporation, Bedford, U.S.A.). The solution (2.0 ml) was poured into each of 1000 vials (10 ml capacity), and lyophilized. Each of the vials was then sealed with a rubber stopper and an aluminum cap. Thus, vials (No. A) each containing 250 mg of the active ingredient were obtained.

A physiological saline solution (2.0 ml) for injections was filled into each of ampoules, and sealed to obtain ampoules (No. B). The physiological saline in the ampoules (No. B) was poured into the vials (No. A) to produce an injection for intravenous administration.

(2) Distilled water (2.0 ml) for injections was poured into the vials (No. A), and the solution was dissolved in a 5% solution of glucose for injections (250 ml). Thus, solutions for drip infusion were prepared.

(3) One thousand vials (No. C) each containing 250 mg of disodium 7-{D-α-[5,8-dihydro-2-(4-formyl-1-piperazinyl)-5-oxopyrido[2,3-d]pyrimidine-6-carboxamido]-α-p-hydroxyphenylacetamido}-3-(5-carboxylatomethyl-1,3,4-thidiazol-2-yl)thiomethyl-3-cephem-4-carboxylate were prepared in the same way as described above.

In Examples 6 to 9 below, the biological activities, water solubilities, and toxicities of Compounds 1 and 2 and A and B shown below were tested.

COMPOUND 1 (the compound of this invention)

Disodium 7-{D-α-[5,8-dihydro-2-(4-formyl-1-piperazinyl)-5-oxopyrido[2,3-d]pyrimidine-6-carboxamido]-α-p-hydroxyphenylacetamido}-3-(1-carboxylatomethyl-1,2,3,4-tetrazol-5-yl)thiomethyl-3-cephem-4-carboxylate

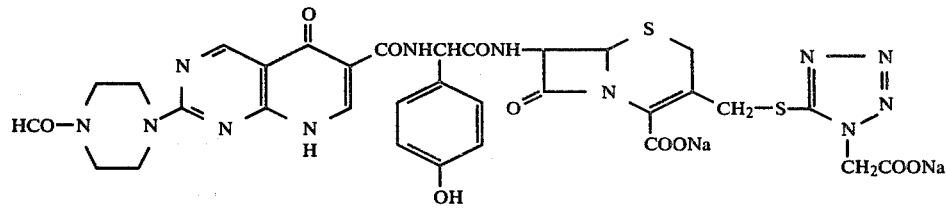

COMPOUND 2 (the compound of this invention)

Disodium 7-{D-α-[5,8-dihydro-2-(4-formyl-1-piperazinyl)-5-oxopyrido[2,3-d]pyrimidine-6-carboxamido]-α-p-hydroxyphenylacetamido}-3-(5-carboxylatomethyl-1,3,4-thiadiazol-2-yl)thiomethyl-3-cephem-4-carboxylate

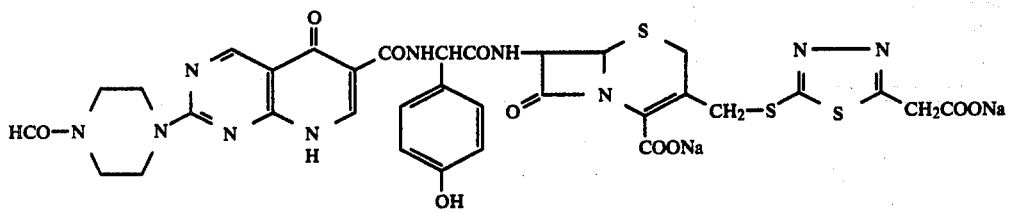

COMPOUND A (the compound disclosed in Belgian Pat. No. 833,063)

Sodium 7-{D-α-[5,8-dihydro-2-(1-piperazinyl)-5-oxopyrido[2,3-d]pyrimidine-6-carboxamido]-α-p-hydroxyphenylacetamido}-3-(1-methyl-1,2,3,4-tetrazol-5-yl)thiomethyl-3-cephem-4-carboxylate

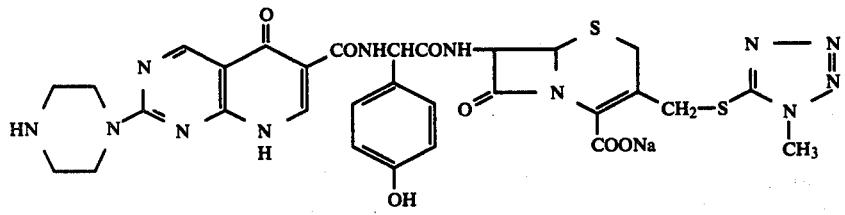

COMPOUND B (the compound disclosed in U.S. Pat. No. 3,516,997)

Cefazolin

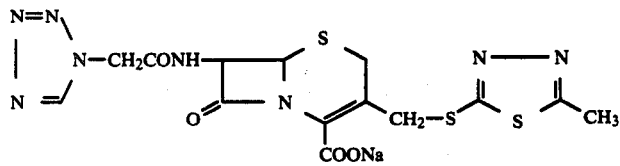

EXAMPLE 6 (in vitro antibacterial activity)

The minimum inhibitory concentrations (μg/ml) of the above compounds against various bacteria in vitro are shown in Table I.

Table I

| | In vitro antibacterial activity against 18 strains of bacteria | | | |
|---|---|---|---|---|
| | Compound | | | |
| Bacteria | 1 | 2 | A | B |
| Staphylococcus aureus 209P JC-1 | 6.25 | 6.25 | 3.13 | 0.2 |
| Staphylococcus aureus No. 50774 | 6.25 | 6.25 | 6.25 | 0.2 |
| Streptococcus pyrogenes 65A | 0.2 | 0.1 | 0.2 | 0.1 |
| Corynebacterium pyrogenes C-21 | 3.13 | 3.13 | 6.25 | 0.39 |
| Escherichia coli NIHJ JC-2 | 1.56 | 0.78 | 1.56 | 1.56 |
| Escherichia coli P-5101 | 0.78 | 0.78 | 0.78 | 1.56 |
| Escherichia coli P-140a* | 1.56 | 1.56 | 1.56 | >200 |
| Salmonella typhimurium S-9 | 1.56 | 1.56 | 0.78 | 1.56 |
| Salmonella enteritidis No. 1891 | 0.78 | 0.78 | 0.78 | 1.56 |
| Shigella flexneri 2a* | 1.56 | 1.56 | 0.78 | 3.13 |
| Shigella flexneri 4a P-330* | 6.25 | 12.5 | 12.5 | >200 |
| Klebsiella pneumoniae No. 13 | 1.56 | 1.56 | 0.78 | 3.13 |

Table I-continued

| | In vitro antibacterial activity against 18 strains of bacteria | | | |
|---|---|---|---|---|
| | Compound | | | |
| Bacteria | 1 | 2 | A | B |
| Enterobacter cloacae P-2540 | 1.56 | 3.13 | 3.13 | >200 |
| Pseudomonas aeruginosa Tsuchijima | 1.56 | 1.56 | 3.13 | >200 |
| Pseudomonas aeruginosa No. 12 | 6.25 | 6.25 | 6.25 | >200 |
| Serratia marcescens IFO 3736 | 3.13 | 6.25 | 6.25 | >200 |
| Proteus morganii Kono | 1.56 | 3.13 | 25 | >200 |
| Proteus mirabilis P-2381 | 0.78 | 1.56 | 12.5 | 6.25 |

Note:
The numerals in the table show minimum inhibitory concentrations (MIC) (μg/ml);
Method: Chemotherapy 22 (6), 1126 (1974)
*Clinically isolated Cephalexin-resistant strain.

EXAMPLE 7 (in vivo therapeutic effect)

Compounds 1, 2, A and B were each dissolved in deionized water to prepare injectable solutions having various concentrations.

Each of the injectable solutions was administered to mice infected with each of the bacteria described below under the conditions described below, and the median effective doses ($ED_{50}$) obtained are shown in Table II.

Experimental conditions

Mice:
  male mice (ddY) weighing about 20 g
Infection:
  (1) Staphylococcus aureus No. 50774; Intravenous infection with 50 to 100 $LD_{50}$ (about $5 \times 10^8$ cells/mouse) of a bacterial suspension in saline.
  (2) Escherichia coli P-5101; Intraperitoneal infection with 50 to 100 $LD_{50}$ (about $9 \times 10^6$ cells/mouse) of a bacterial suspension in trypto-soy broth with 4% mucin.
  (3) Pseudomonas aeruginosa No. 12; Intraperitoneal infection with 50 to 100 $LD_{50}$ (about $5 \times 10^3$ cells/- mouse) of a bacterial suspension in trypto-soy broth with 4% mucin.

Medication:

twice, about 5 minutes and 6 hours after infection.

Observation:

| Staphylococcus aureus No. 50774 | 14 days |
| Escherichia coli P-5101 | }  7 days. |
| Pseudomonas aeruginosa No. 12 | |

Table II

| | In vivo efficacy against systemic infection. | | | |
|---|---|---|---|---|
| Bacterium | Staphylococcus aureus | Escherichia coli | Pseudomonas aeruginosa | |
| Route | No. 50774 | P-5101 | No. 12 | |
| Compound | sc | sc | sc | po |
| 1 | 13.1 | 1.5 | 4.8 | >100 |
| 2 | 11.5 | 2.5 | 9.6 | >100 |
| A | about 7.8 | about 0.4 | 4.8 | >100 |
| B | 0.2 | 5.3 | >800 | >100 |

Note: The numerals in the table show $ED_{50}$ (mg/kg). $ED_{50}$ values were calculated in accordance with the Behrens-Kaerber method (Arch. Exp. Path. Pharm., 162, 480 (1931)).

sc: subcutaneous administration
pc: peroral administration.

EXAMPLE 8 (acute toxicity

Injectable solutions containing compounds 1, 2 and compound A in various concentrations were administered to male mice (ddY) (4 to 8 in each group) in a dose of 0.1 ml per 10 g of body weight. The number of dead mice was counted after a lapse of 7 days, and the value of median lethal dose ($LD_{50}$, mg/kg) was calculated. The results are shown in Table III.

Table III

| | Acute toxicity in mice. | |
|---|---|---|
| Compound No. | Route | $LD_{50}$ (mg/kg) |
| 1 | iv | >2000 |
| 2 | iv | >2000 |
| A | ip | about 1500 |

Note: The $LD_{50}$ values were calculated in accordance with the Behrens-Kaerber method.
iv: intravenous administration
ip: intraperitoneal administration.

EXAMPLE 9 (solubility in water)

Table IV

| Solubility in deionized water at 25° C. | |
|---|---|
| Compound No. | Solubility (mg/ml-water) |
| 1 | about 400 |
| 2 | about 150 |
| A | about 0.5 |

Table IV-continued

| Solubility in deionized water at 25° C. | |
|---|---|
| Compound No. | Solubility (mg/ml-water) |
| B | 400 |

Note: The hydrochloride and potassium salt corresponding to compound A are soluble in deionized water in the same degree as compound A.

What we claim is:

1. A member selected from the group consisting of cephalosporin compounds of the formula

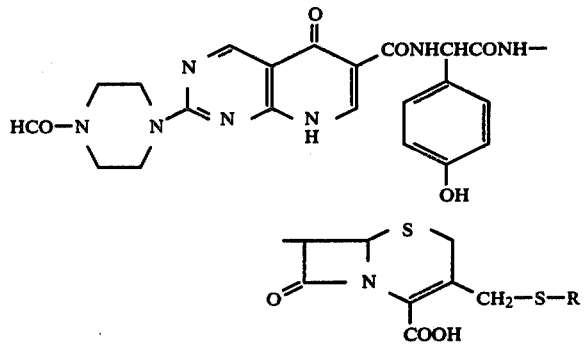

wherein R is 1-carboxymethyl-1,2,3,4-tetrazol-5-yl or 5-carboxymethyl-1,3,4-thiadiazol-2-yl,
and non-toxic pharmaceutically acceptable salts thereof.

2. A member selected from the group consisting of a cephalosporin compound of the formula

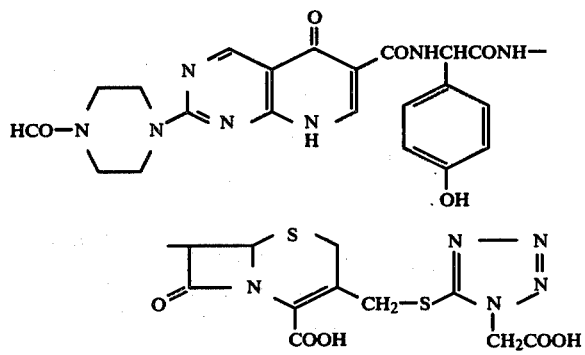

and a non-toxic pharmaceutically acceptable salt thereof.

3. A member selected from the group consisting of 7-{D-α-[5,8-dihydro-2-(4-formyl-1-piperazinyl)-5-oxopyrido[2,3-d]pyrimidine-6-carboxamido]-α-p-hydroxyphenylacetamido}-3-(1-carboxymethyl-1,2,3,4-tetrazol-5-yl)thiomethyl-3-cephem-4-carboxylic acid and an alkali metal salt thereof.

4. A member selected from the group consisting of a cephalosporin compound of the formula

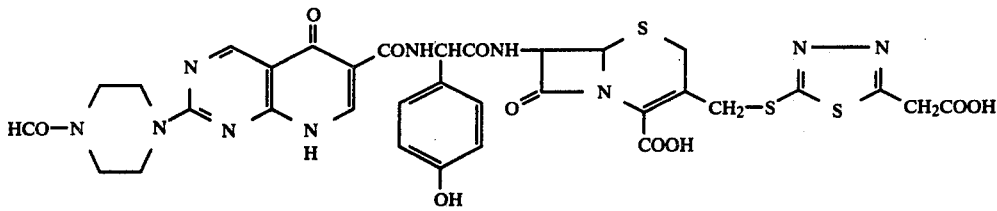

and a non-toxic pharmaceutically acceptable salt thereof.

5. A member selected from the group consisting of 7-{D-α-[5,8-dihydro-2-(4-formyl-1-piperazinyl)-5-oxopyrido[2,3-d]pyrimidine-6-carboxyamido]-α-p-hydroxyphenylacetamido}-3-(5-carboxymethyl-1,3,4-thiadiazol-2-yl)thiomethyl-3-cephem-4-carboxylic acid and an alkali metal salt thereof.

6. A parenteral, antibacterial solution comprising an antibacterially effective amount of a member selected from the group consisting of a cephalosporin compound of the formula

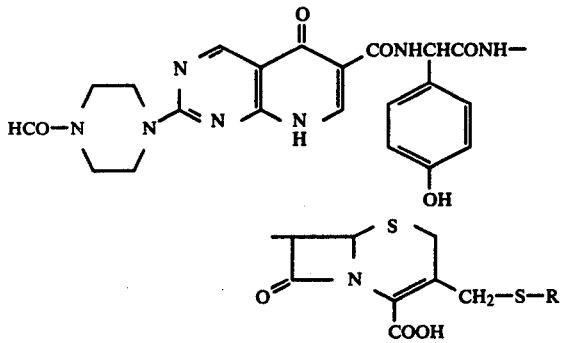

wherein R is 1-carboxymethyl-1,2,3,4-tetrazol-5-yl or 5-carboxymethyl-1,3,4-thiadiazol-2-yl,
and a non-toxic pharmaceutically acceptable salt thereof, in a nontoxic liquid medium.

7. The solution of claim 6 wherein the member is 7-{D-α-[5,8-dihydro-2-(4-formyl-1-piperazinyl)-5-oxopyrido[2,3-d]pyrimidine-6-carboxamido]-α-p-hydroxyphenylacetamido}-3-(1-carboxymethyl-1,2,3,4-tetrazol-5-yl)thiomethyl-3-cephem-4-carboxylic acid or an alkali metal salt thereof.

8. The solution of claim 6 wherein the member is 7-{D-α-[5,7-dihydro-2-(4-formyl-1-piperazinyl)-5-oxopyrido[2,3-d]pyrimidine-6-carboxamido]-α-p-hydroxyphenylacetamido}-3-(5-carboxymethyl-1,3,4-thiadiazol-2-yl)thiomethyl-3-cephem-4-caroboxylic acid or an alkali metal salt thereof.

9. A method for treating bacterial infections which comprises parenterally administering an antibacterially effective dose of the compound defined in claim 1 to a warm-blooded animal.

10. An injectable composition which comprises an antibacterially effective amount of a member selected from the group consisting of a cephalosporin compound of the formula

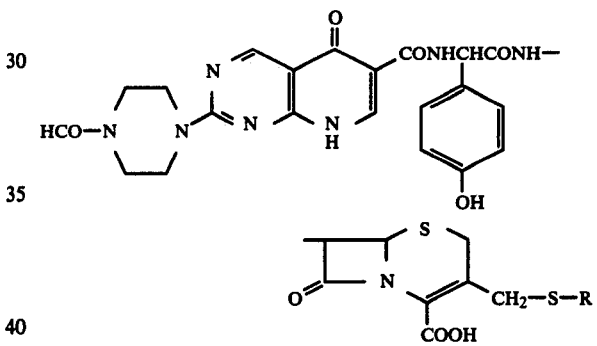

wherein R is 1-carboxymethyl-1,2,3,4-tetrazol-5-yl or 5-carboxymethyl-1,3,4-thiadiazol-2-yl,
and a non-toxic pharmaceutically acceptable salt thereof and a pharmaceutically acceptable carrier therefor.

* * * * *